United States Patent [19]

Morra et al.

[11] Patent Number: 6,129,956
[45] Date of Patent: Oct. 10, 2000

[54] PROCESS FOR THE COATING OF OBJECTS WITH HYALURONIC ACID, DERIVATIVES THEREOF, AND SEMISYNTHETIC POLYMERS

[75] Inventors: Marco Morra; Clara Cassinelli, both of Asti; Luca Benedetti; Lanfranco Callegaro, both of Vicenza, all of Italy

[73] Assignee: Fidia Advanced Bioplymers, Srl, Brindisi, Italy

[21] Appl. No.: 08/930,858

[22] PCT Filed: Feb. 7, 1996

[86] PCT No.: PCT/EP96/00509

§ 371 Date: Oct. 7, 1999

§ 102(e) Date: Oct. 7, 1999

[87] PCT Pub. No.: WO96/24392

PCT Pub. Date: Aug. 15, 1996

[30] Foreign Application Priority Data

Feb. 7, 1995 [IT] Italy ................................ PD95A0030
Dec. 20, 1995 [IT] Italy ................................ PD95A0243

[51] Int. Cl.$^7$ ................................................. B05D 3/06
[52] U.S. Cl. ........................... 427/535; 427/387; 427/409; 427/412.1
[58] Field of Search ................. 427/409, 412.1, 427/412.3, 387, 535

[56] References Cited

U.S. PATENT DOCUMENTS 4,657,820  4/1987  Halpern et al. .
4,663,233  5/1987  Beavers .
4,722,867  2/1988  Halpern et al. .
4,801,475  1/1989  Halpern et al. .

(List continued on next page.)

FOREIGN PATENT DOCUMENTS

138572A2  4/1985  European Pat. Off. .
138572B1  4/1985  European Pat. Off. .
216453A2  1/1987  European Pat. Off. .
216453B1  4/1987  European Pat. Off. .

(List continued on next page.)

OTHER PUBLICATIONS

Joshi, H. N. et al, "Hydration in hyaluronic acid and its esters using differential scanning calorimetry", International Journal of Pharmaceuticetics, 80 (1992), pp. 213–225.

Gregorius, K. et al, "Hydrocating: A new method for coupling biomolecules to solid phases", Journal of Immunological Methods, 181 (1995) pp. 65–73.

Scott, John E. et al, "Periodate Oxidation and the shapes of Glycosaminoglycuronans in Solution", Biochem. J., 173 (1978) pp. 103–114.

Staros, James V. et al, "Enhancement by N–Hydroxysulfosuccinimide of Water–Soluble Carbodiimide–Mediated Coupling Reactions", Analytical Biochemistry, 156 (1986) pp. 220–222.

Silver, Frederick H. et al, "Physical Properties of Hyaluronic Acid and Hydroxypropylmethylcellulose in Solution: Evaluation of Coating Ability", Journal of applied Biomaterials, 5 (1994) pp. 89–98.

Nygren, Hakan et al, "Covelent binding of neutral polysaccharides to surfaces reduces platelet adhesion and fibrin–clot formation during initial contact with blood", Acta Physiol Scand, 116 (1982) pp. 201–203.

(List continued on next page.)

*Primary Examiner*—Erma Cameron
*Attorney, Agent, or Firm*—Birch, Stewart, Kolasch & Birch, LLP

[57] ABSTRACT

Processes are provided for coating the surfaces of objects with hyaluronic acid, its derivatives or other natural or semisynthetic polymers, for applications in the fields of surgery, health care and diagnostics. The processes make it possible to bind such polymers in a stable manner to the surfaces of objects made of a wide range of materials. Surfaces treated according to the processes are characterized by a high degree of wettability, and are able to inhibit the adhesion of cells or bacteria present in the biological fluids.

22 Claims, 9 Drawing Sheets

U.S. PATENT DOCUMENTS

| | | |
|---|---|---|
| 4,810,586 | 3/1989 | Halpern et al. . |
| 4,810,784 | 3/1989 | Larm . |
| 4,851,521 | 7/1989 | Della Valle et al. . |
| 4,959,074 | 9/1990 | Halpern et al. . |
| 5,023,114 | 6/1991 | Halpern et al. . |
| 5,037,677 | 8/1991 | Halpern et al. . |
| 5,080,924 | 1/1992 | Kamel et al. .............................. 427/2 |
| 5,132,108 | 7/1992 | Narayanan et al. ................. 427/78.17 |
| 5,244,654 | 9/1993 | Narayanan ........................... 424/78.17 |
| 5,308,641 | 5/1994 | Cahalan et al. ............................ 427/2 |
| 5,356,433 | 10/1994 | Rowland et al. ......................... 623/11 |
| 5,409,696 | 4/1995 | Narayanan et al. . |
| 5,668,193 | 9/1997 | Gouda et al. ........................... 523/112 |

FOREIGN PATENT DOCUMENTS

| | | |
|---|---|---|
| 233708A3 | 8/1987 | European Pat. Off. . |
| 251905A2 | 1/1988 | European Pat. Off. . |
| 251905B1 | 1/1988 | European Pat. Off. . |
| 265116A2 | 4/1988 | European Pat. Off. . |
| 265116B1 | 4/1988 | European Pat. Off. . |
| 341745A1 | 11/1989 | European Pat. Off. . |
| 341745B1 | 11/1989 | European Pat. Off. . |
| 342557A1 | 11/1989 | European Pat. Off. . |
| 342557B1 | 11/1989 | European Pat. Off. . |
| 518710A1 | 12/1992 | European Pat. Off. . |
| 518710B1 | 12/1992 | European Pat. Off. . |
| 094924A3 | 11/1998 | European Pat. Off. . |
| 19630879 | 2/1998 | Germany . |
| 4126074A | 4/1992 | Japan . |
| WO 9306136 | 4/1993 | WIPO . |
| WO 9314129 | 7/1993 | WIPO . |
| WO 9403499 | 2/1994 | WIPO . |
| WO 9406485 | 3/1994 | WIPO . |

OTHER PUBLICATIONS

Xu, X. et al, The Use of $^2$H–NMR for Probing the Structure of Chemically Modified Sodium Hyaluronate, *Fourth World Biomaterials Congress*, Berlin, Federal Republic of Germany, Apr. 24–28, 1992, p. 170.

Garbassi, Fabio et al, *Polymer Surfaces: From Physics to Technology*, 1994, p. 304.

Brink et al., "Using poly(ethylene imine) to graft poly(ethylene glycol) of polysaccharide to polystyrene" *Colloids and Surfaces* 66 (1992), pp. 149–156.

Kvam et al, "$^1$H– and $^{13}$C–NMR studies of solutions of hyaluronic acid esters and salts in methyl sulfoxide: comparsion of hydrogen–bond patterns and conformational behavior", *Carbohydrate Research*, 230 (1992), pp. 1–13.

Kaufman et al., "Corneal Endothelium Damage with intraocular Lenses: Contct Adhesion Between Surigical Materials and Tissue", *Science*, vol. 198 (Nov. 1998), pp. 525–527.

Narayanan et al., "Surface functionalization by RF plasma treatment of polymers for immobilization of bioactive–molecules", *J. Biomater. Sci. Polymer Edn*, vol. 6, No. 2 (1994), pp. 181–193.

Osterberg et al., "Protein–rejecting ability of surface–bound dextran in end–on and side–on configuration: Comparison to PEG", *Journal of Biomedical Materials Research*, vol. 29 (1995), pp. 741–747.

Elam et al., "Coalent coupling of polysaccharides to silicon and silicon rubber surfaces", *Journal of Biomedical Materials Research*, vol. 18 (1984), pp. 953–959.

JP 59183762 Sep. 25, 1993–Abstract.

PROCESS FOR THE COATING OF OBJECTS WITH HYALURONIC ACID, DERIVATIVES THEREOF, AND SEMISYNTHETIC POLYMERS

This application is the national stage of International Application No. PCT/EP96/00509, filed Feb. 7, 1996.

FIELD OF THE INVENTION

The present invention concerns processes of coating the outer surfaces of objects with hyaluronic acid and its derivatives or other natural or semisynthetic polymers for applications in the fields of surgery, health care and diagnostics. According to this process it is possible to bind the polymer in a stable manner to the surfaces of objects made of a wide range of materials. Surfaces treated by the processes described in the present invention are characterized by a high degree of wettability and slipperiness in an aqueous environment, and improved properties in interactions with biological phases. For example, they are able to inhibit the adhesion of cells or bacteria present in the biological fluids.

BACKGROUND OF THE INVENTION

Hyaluronic acid is a natural mucopolysaccharide present at varying concentrations in practically all tissues. As any expert in the art knows, aqueous solutions of hyaluronic acid or of the salts or derivatives thereof, or of polysaccharides in general, are characterized by notable viscosity, slipperiness, and ability to reduce friction, a characteristic which is at the basis of the presence and function of polysaccharides of the same family as hyaluronic acid in the bodies of humans and other animals (Michels R. G. et al., "Sodium hyaluronate in anterior and posterior segment surgery". Physicochemical and Pharmacological Characteristics of Hyaluronic Acid, 1–15, 1989)

Because of these qualities, polysaccharides of the same family as hyaluronic acid (both natural polysaccharides and those obtained by chemical synthesis on natural compounds) have been widely researched. In particular, great effort has been put into identifying methods by which thin layers of hyaluronic acid (Hyalectin fraction, as described in European patent No. 0138572) or the derivatives thereof (U.S. Pat. No. 4,851,521) can be permanently fixed to the surface of other materials. The aim of this research was to create objects with improved surface properties, while maintaining the overall characteristics of the material of which they are made (said material will hereafter be referred to as the substrate). In particular, because of their high degree of hydrophilia, hyaluronic acid and the derivatives thereof are especially suitable for making objects whose use requires that their surfaces resist adhesion to the cell species present in the tissues or biological fluids. Such surfaces are of particular interest in applications wherein adhesion between materials and cells can cause damage to biological tissues (Kaufman, H. E. et al., Science, 189, 525, 1977).

Modification of the surfaces of materials with hyaluronic acid or the derivatives thereof has proved difficult for many researchers. One of the first things one notices is that hyaluronic acid solutions have a rather high surface tension, the same as or slightly less than that of water (F. H. Silver et al., Journal of Applied Biomaterials, 5, 89, 1994). It is well known that to obtain a homogeneous coating by the application of a solution, the applied material must have a surface tension which is lower than that of the substrate in order to obtain complete, even coverage. Moreover, almost all polymer materials which can be used as substrates present a surface tension which is lower than that of water, a characteristic which prevents the formation of a thin layer of hyaluronic acid covering the substrate evenly (Garbassi F. et al., "Polymer Surfaces, from Physics to Technology", Wiley, Chichester, 304, 1994).

It should be noted that hyaluronic acid is water soluble, so any objects obtained by simply coating them with a layer of hyaluronic acid solution instantly lose their coating on contact with aqueous solutions, including biological fluids. Hyaluronic acid derivatives, even those which are not water soluble, are in any case extremely hydrophilic and have a strong tendency to swell in the presence of water or aqueous solutions (H. N. Joshi and E. M. Topp, International Journ. of Pharm. 80 (1992) 213–225). In aqueous environments, this characteristic rapidly causes the detachment of the hydrophilic surface layer applied to the substrate by a simple coating process using a solution. For these reasons, methods involving a chemical bond between the substrate surface and hyaluronic acid or its derivatives have been studied.

The presence of a stable chemical bond prevents the surface layer from being dissolved and lends stronger, longer-lasting surface properties to the object. The realization of a chemical bond between the substrate and the surface layer requires the presence of suitable chemical groups in both. While the chemical structure of hyaluronic acid ensures the presence of various suitable functions, the surface of most synthetic materials is not particularly suitable for this type of operation. For this reason, processes for the creation of a chemical bond between a surface layer of hyaluronic acid or its derivatives and a synthetic substrate usually consist of two steps. In the first step suitable chemical groups are introduced onto the surface, then in the second step, a reaction is induced between the chemical groups introduced onto the substrate surface and hyaluronic acid or its derivatives. For example, U.S. Pat. Nos. 4,657,820, 4,663,233, 4,722,867, 4,801,475, 4,810,586, 4,959,074, 5,023,114 and 5,037,677 describe the use of an intermediate layer between the substrate and the hyaluronic acid coating. This intermediate layer physically adheres to the substrate and contains chemical groups which are suitable for the formation of a bond with the chemical groups of hyaluronic acid. To facilitate spreading and ensure even coating of the substrate by the hyaluronic acid, the aforesaid patents also describe the use of albumin which, when added to hyaluronic acid, improves its ability to dampen the intermediate layer evenly.

Other documents describe the use of plasma technology to introduce reactive groups onto the substrate. This technique (Garbassi F. et al., "Polymer Surfaces, from Physics to Technology", Wiley, Chichester, 6, 1994), makes it possible to modify the surface of polymer materials in a fast, effective manner. For instance, international patent application No. WO 94/06485, describes the introduction of functional groups onto the surface of a polymeric material by treatment with methanol plasma. The treated material is then placed in contact with an epihydrochlorine solution which guarantees the presence of groups suited to reaction with polysaccharides.

Other articles (Acta Physiologica Scandinava, 116, 201, 1982; Journal of Biomedical Materials Research, 18, 953, 1984, Elan et al.) describe a treatment with oxygen plasma, followed by the application of 3-glycidoxypropyltrimethoxy silane. Surfaces thus treated are used for the formation of covalent bonds with polysaccharides.

Although the above described methods are generally satisfactory, they nonetheless each present some difficulties.

In particular, the use of an intermediate layer calls for its composition to be adapted to the nature of the substrate, so as to enhance adhesion as much as possible. In the case of the production of objects constituted by new materials, or materials which are rarely used, much time and effort is taken up in identifying the most suitable formulation for the intermediate layer. If the objects to be coated are composed of different materials, it is difficult to apply a suitable intermediate layer for each component while avoiding overlapping and protrusion of the intermediate layers in unsuitable places. Moreover, it may be undesirable to use albumin to enhance the wettability of the substrate, especially in the case of products intended for biomedical applications.

Regarding the other examples cited, it is preferable to avoid using epihydrochlorine and 3-glycidoxypropyltrimethoxy silane, as these two compounds are known to be major health hazards. Indeed, according to the classification of dangerous substances issued by the European Union, these compounds are coded as "R45" and "R40" respectively, signifying a health risk, as reported in most catalogues for chemical products and reagents. This designation indicates, in the first case, that the product can cause cancer, and in the second case that there is a risk of irreversible effects.

More generally, the total number of reactions which involve functional groups immobilized on a surface and large molecules, such as polysaccharides, is seriously limited by the effect commonly known as steric hindrance. The large size of the polysaccharide molecule prevents or impedes contact between reactive groups so that the probability of an effective reactive encounter is decidedly low.

Other methods described in the art involve the reaction between polysaccharides and amino groups. Japanese patent JP 04126074 (Apr. 27, 1992) describes the use of treatment with ammonia plasma to introduce amino groups on the surface of polymer substrates. The amino groups are then reacted with hyaluronic acid or other polysaccharides by the use of a condensing agent. In U.S. Pat. No. 4,810,784, the surface of an object made of polymer material is treated with reactive solutions, so as to introduce negative electrostatic charges onto the surface itself. The surface thus treated is placed in contact with an aqueous solution of polyethylene imine (PEI), a polymer characterized by the presence of amino groups and a positive electrostatic charge. The interaction between the different charges binds PEI to the modified surface, to produce a surface rich in amino groups. Heparin and other polysaccharides are bound to the aminated surface after treatment with nitrite solutions. It is a known fact in organic chemistry that the action of nitrites causes the formation of aldehyde groups. These react with the aminated surface, binding the polysaccharide irreversibly to the surface itself. The same reaction is used when aldehyde groups are introduced by bland oxidation with periodate (C. Brink et al., "Colloids and Surfaces", 149, 66, 1992).

The reaction between PEI and any aldehyde groups present or introduced on the polysaccharide is, moreover, sometimes used to bind the polysaccharide, in various conformations, to the surface of the object (E. Ostenberg et al., Journal of Biomedical Materials Research, 29, 741, 1995). U.S. Pat. No. 5,409,696 describes the modification of the surface of materials by treatment with plasma containing water vapor and the subsequent reaction of the treated surface with PEI. The surface thus obtained is rich in amino groups and is able to bind heparin and other polysaccharides irreversibly by the action of condensing agents. Typically, the reaction between carboxy groups of the polysaccharide and amino groups of the surface is promoted by ethyldimethylaminopropyl-carbodiimide (EDC). The use of this process to coat the insides of tubes intended to come into contact with the blood has been described by P. V. Narayanan (Journal of Biomaterials Science, Polymer Edition, 6, 181, 1994).

Research has shown that the processes described in the cited patents and articles are not entirely satisfactory as far as the making of objects with surfaces modified by hyaluronic acid or its derivatives is concerned. Indeed, the introduction of amino-type functional groups by means of ammonia plasma, as described in Patent No. JP 04126074 (Apr. 27, 1992), is not very practical in a production process. Experts in the field know that the density of the functional groups introduced by this technique onto the surface of the substrate is rather low, and depends too much on the precise geometry of the reactor used for the plasma treatment, on the nature of the substrate, on the presence of additives and/or contaminants on the surface of and inside the substrate and on the storage conditions of the substrate before and after treatment. For this reason the technique is difficult to apply to industrial production. This negative aspect is recognized by those working in the field and, in the above-noted U.S. Pat. Nos. 4,810,874 and 5,409,696, it is counteracted by using PEI, which allows a high density of amino groups to be obtained. Although these last processes effectively solve the problems involved in the first stage of the process, that is the introduction of reactive groups on the surface of the material, they are not so effective in the second stage, which involves binding hyaluronic acid or derivatives thereof to the surface. Indeed, as we said previously, U.S. Pat. No. 4,810,874 recommends the activation of heparin or other polysaccharides by chemical treatment. It is not, therefore, possible to use the polysaccharide as such, but it is necessary to first modify it by a chemical operation, incurring extra costs in terms of time, reagents, labor and refuse disposal. Moreover, unlike other polysaccharides, hyaluronic acid is only slightly sensitive to the partial oxidation reactions which allow reactive aldehyde-type groups to be introduced on the polysaccharide (J. E. Scott and M. J. Tigwell, Biochem. J., 173, 103, 1978; B. J. Kvam et al., Carbohydrate Research, 230, 1, 1992). As far as U.S. Pat. No. 5,409,696 is concerned, when the process proposed therein is carried out, it does not produce a surface structure able to exploit to the fullest extent the intrinsic characteristics of hyaluronic acid. When the process described in U.S. Pat. No. 5,409,696 is used, on the other hand, as shown in the comparative testing set forth herein, it is not possible to obtain surface structures able to inhibit cell adhesion. Similar results are observed when, instead of hyaluronic acid itself, its water-soluble semisynthetic esters are used (EPA 0216453). Evidently, when this process is used, the way in which a bond is formed between the aminated surface and polysaccharide does not allow the hydrophilic characteristics of hyaluronic acid or its derivatives to be exploited to the fullest extent.

It must not be overlooked that the process which is the subject of U.S. Pat. No. 5,409,696 can be applied only in the surface modification of polymer materials, as indicated by its title "Radio frequency plasma treated polymeric surfaces having immobilized antithrombogenic agents" and by the operational instructions thereof. In common biomedical and surgical practice, ceramic or metallic materials are frequently used, so it is hoped that the modification processes can be applied to such substrates too. This description demonstrates that a method must be devised whereby a chemical bond can be formed, simply and reliably, between substrates of any nature and hyaluronic acid or its derivatives, in such a way that the intrinsic characteristics thereof can be exploited to the fullest extent possible.

SUMMARY OF THE INVENTION

The present invention particularly concerns processes of coating biomedical objects with a thin layer of hyaluronic acid, a derivative thereof, or a semisynthetic polymer, wherein the thin layer is linked stably to an underlying material. In this way a composite structure is made, the body of which is characterized by the properties of the material used to make the object, while its surface characteristics are those of the thin layer of hyaluronic acid, its derivative, or said semisynthetic polymer. Said characteristics can confer a high degree of hydrophilia to the surfaces of the materials treated according to the processes of the present invention. For example, the surfaces of the objects treated according to the processes of the present invention are able to prevent the adhesion of cells present in the biological fluids and to reduce bacterial adhesion. Moreover, coating an object with a material of natural origin according to the present invention ensures better properties in interactions with biological phases.

BRIEF DESCRIPTION OF THE DRAWINGS

The present invention will become more fully understood from the detailed description given hereinbelow and the accompanying drawings which are given by way of illustration only, and, thus, are not limitative of the present invention, and wherein.

DETAILED DESCRIPTION OF THE INVENTION

Figure 1A:
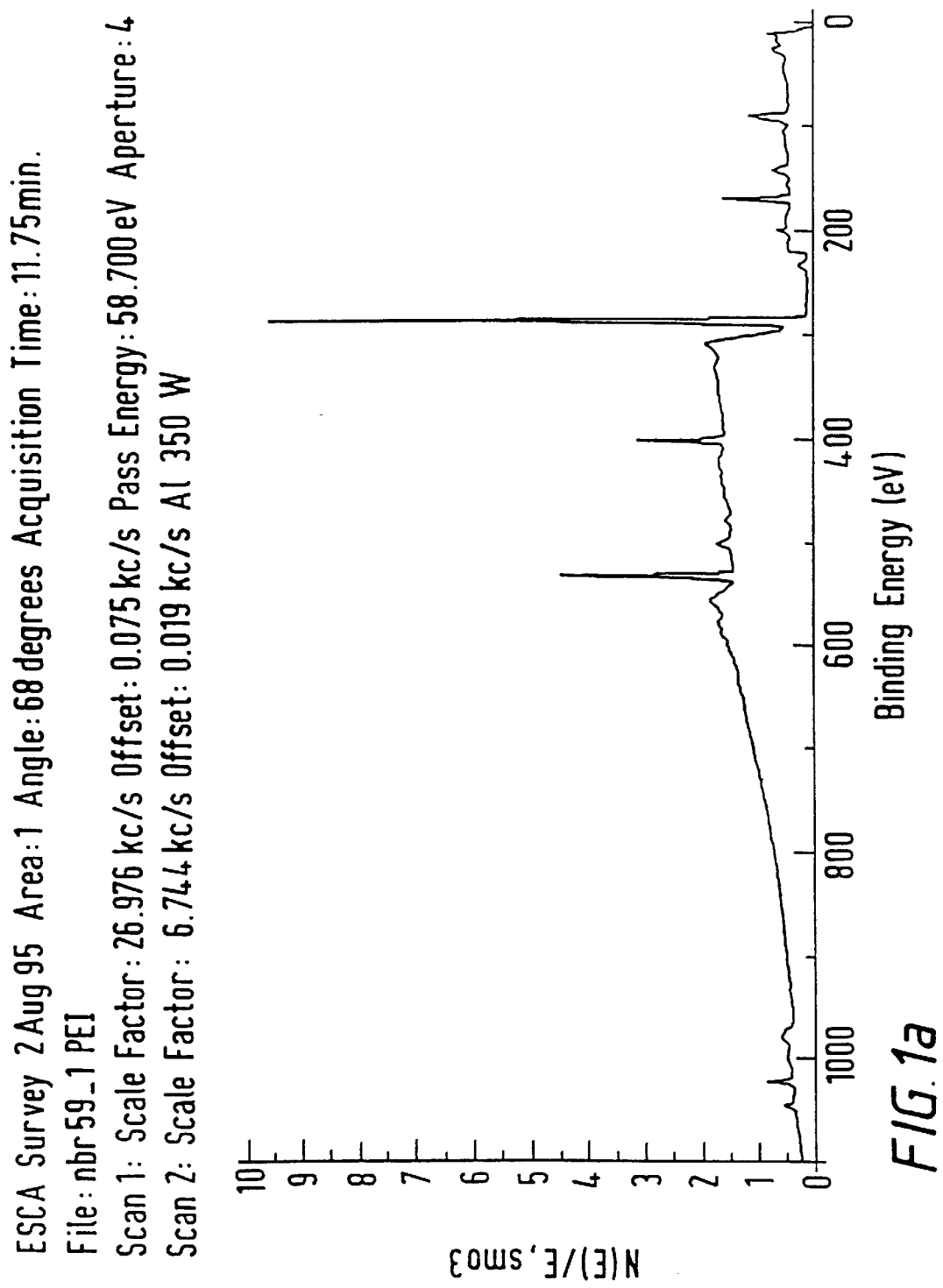
FIG. 1a: ESCA spectrum of sample 1, Example 1

Other objects and further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

In general terms, the present invention provides for the coating of an object with a layer of hyaluronic acid, or a derivative thereof (e.g., such as a polysaccharide containing carboxyl groups), or a semisynthetic polymer such as described below, by the formation of a chemical bond with the surface of the substrate. The inventors have discussed two distinct inventive processes that are advantageous and are part of the present discovery. These are referred to below as "Process A" and "Process B", respectively.

In both Process A and B of the present invention, as an alternative to hyaluronic acid, or its derivatives (such as its partial derivatives (EPA 0216453) or polysaccharides containing carboxy groups), it is possible to apply the above-noted processes to various semisynthetic polymers, such as esters of polyvalent alcohols of hyaluronic acid (EP 0265116), inner esters of acidic polysaccharides (EPA 0341745), esters of carboxy-methylcellulose, carboxymethylchitin and carboxy-methylamide (EP 0342557), active esters of carboxy polysaccharides (Italian patent application No. PD 94A000043), sulfated esters of hyaluronic acid (Italian patent application No. PD 94000054), esters of alginic acid (EP 0251905), gellan esters (EPA 0518710), inner esters of gellan (WO 94/03499), esters of chitin and chitosan (EPA 0603264), esters of pectic and pectinic acid (EPA 0621877).

Process A

Process A of the present invention provides a new process for the coating of an object with a layer of hyaluronic acid, or a derivative thereof, or a semisynthetic polymer, by the formation of a chemical bond with the substrate surface. In contrast to known and previously described processes, which involved the reaction of functional groups on polysaccharide macromolecule and functional groups present on the surface with the previously mentioned problem of low yields, the present invention provides for an inventive process that can be performed in two steps and avoid problems associated with the prior known and described processes.

In the first step of the inventive Process A, hyaluronic acid, a derivative thereof, or a semisynthetic polymer is reacted with a suitable compound, which is an alkoxy silane coupling agent, exclusively in a solution. By eliminating in this first step the need for a reaction with functional groups fixed on the surface of the substrate ( and therefore practically immobile), it is possible to reduce the negative effect of steric hindrance of the polysaccharide molecule in the first step of the reaction process.

In the second step of the inventive Process A, the reaction product of the reaction between the hyaluronic acid, the derivative thereof, or the semisynthetic polymer and the alkoxy silane coupling agent is applied in the form of a solution to the substrate surface, according to normal physical coating methods. A bond then forms between the alkoxy silane moiety of said reaction product and the substrate during elimination of solvent from the coating solution, when the coating solution is in contact with the substrate and the probability of a reaction taking place is very high. Experiments have shown that the efficacy of Process A is surprisingly higher, when it is conducted in the two described steps, compared to when traditional methods described in the art are used, namely those involving the reaction between functional groups immobilized on a surface and functional groups present in a polysaccharide macromolecule.

Accordingly, in Process A of the present invention hyaluronic acid, a derivative thereof, or a semisynthetic polymer is reacted in an aqueous solution, or generally, in a suitable solvent with an alkoxy silane coupling agent molecule which can bind to the hyaluronic acid, the derivative thereof, or said semisynthetic polymer at one extremity and to the substrate at the other.

As noted, in Process A of the invention the hyaluronic acid, a derivative thereof, or a semisynthetic polymer is reacted with a compound belonging to the class of alkoxy silanes. These compounds are known to experts in the chemical art as coupling agents that can be used to enhance the adhesion properties between organic and inorganic materials ("Silane Coupling Agents"), E. P. Plueddemann, Plenum Press, New York, 1982). Exemplary of such alkoxy silane coupling agents are molecules containing halogens such as chloropropyltrimethoxy silane, molecules containing unsaturated organic groups such as vinyltriethoxy silane and methacryloxypropyltrimethoxy silane, molecules containing hydrosulfide groups such as mercaptopropyltrimethoxy silane, molecules containing amino groups such as aminopropyltrimethoxy silane and aminoethylaminopropyltrimethoxy silane. However, the inventive process is not limited to such specific types of alkoxy silane coupling agents.

In Process A of the invention, the reaction between the hyaluronic acid, the derivative thereof, or the semisynthetic polymer and the alkoxy silane may require the use of one or more molecules which allow for the reaction between functional groups of the hyaluronic acid, the derivative thereof, or the semisynthetic polymer and the functional groups of alkoxy silane. This class of molecule includes, among others, compounds belonging to the diimide group, which come under the generic definition of condensing agents, such as cyclohexylcarbodiimide and ethyldiaminopropylcarbodiimide, and all those compounds such as carbonyldiimidazol and dicarbonyldiimidazol which are defined as bifunctional agents, known to operators in the field for the synthesis of protein compounds. Molecules which catalyze or facilitate the reaction between functional groups of hyaluronic acid or a derivative thereof and functional groups of alkoxy silane may also be used in the inventive process. Some illustrative examples are N-hydroxysuccinimide, hydroxysulfosuccinimide, 1-hydroxybenzotriazol hydrate and similar compounds thereto serving the same function. It is noted that the use of such compounds is also provided for in Process B of the present invention, as described below.

In Process A, the substrate to be coated is adapted by means of a plasma treatment in order to better react with the reaction product thus formed, containing the hyaluronic acid, the derivative thereof, or the semisynthetic polymer. Without wishing to be limited to a specific theory, it is thought that plasma treatment of the substrate has the effect of increasing the surface tension of the substrate, so as to uniformly enhance wettability by the solution containing hyaluronic acid and alkoxy silane and the other molecules. Moreover, it allows functional groups able to enhance the reaction with the alkoxy silane to be introduced onto the substrate surface. In particular, treatments that introduce hydroxy, carboxy groups will be used and, generally, those functions defined as acid in commonly accepted chemical terms. As there are many chemical functions able to enhance the reaction between the substrate surface and the silane coupling agent, the conditions of treatment by plasma are far less restrictive than in the case of the treatments currently described in the art. Some examples of suitable treatments are those using plasma of oxygen, air, nitrogen, argon and other rare gases, water, alcohols and mixtures of the cited gases or vapors. The nature of the substrate is not limiting and is only conditioned by the possibility of generating, after plasma treatment, superficial functional groups able to enhance the reaction with silane.

In one particularly favorable form of the present inventive Process A, the reaction between hyaluronic acid or a derivative thereof and the alkoxy silane coupling agent occurs in an aqueous solution, with the hyaluronic acid or derivative thereof being in a concentration of between 0.01 and 2% and preferably between 0.1 and 1.2%. The alkoxy silane is preferably an amino silane present in a stoichiometric quantity, calculated according to the reaction plan or slightly in excess thereof. In such preferred instances, the reaction solution preferably also contains ethyldiaminopropylcarbodiimide, in a stoichiometric quantity calculated according to the reaction between the carboxy groups available on the hyaluronic acid or derivative thereof and the amino group of amino silane, or slightly in excess thereof. The reaction is assisted by the presence of N-hydroxysuccinimide in a quantity of between 10 and 100% compared to the molar concentration of the carbodiimide. After several hours' reaction at room temperature, the solution is applied to the surface of the object, which has just been treated with plasma, according to the methods normally used for the application of thin surface layers of a solution. The plasma treatment is preferably performed with an oxygen or air plasma, with a power charge of between 1 and 400 W, preferably between 10 and 150 W, a pressure between 10 mtorr and 10 torr, and a treatment time between 1 second and 1 hour, preferably between 10 seconds and 30 minutes. The solvent is evaporated with or without the aid of a vacuum and with or without the aid of heat. Operations at this stage depend upon the necessity to create the necessary conditions to allow the reaction between the reactive terminations of the alkoxy silane coupling agent and the functional groups present on the substrate surface after plasma treatment. At the end of operations, any reaction residues and molecules which are not stably bound may be removed by further washing or using a similar method.

Process B

According to a separate embodiment of the present invention, a substrate material, of any kind, is treated with plasma of air, oxygen, argon, nitrogen or other gases or vapors able to introduce oxygenated functions to the surface and/or to exercise a cleansing effect and the removal of organic contaminants. However, the use of a plasma containing water vapor, as claimed in U.S. Pat. No. 5,409,696, is not required in such processes of the present invention.

The surface of the material thus treated is exposed to an aqueous solution of PEI (or another polycationic substance such as polylysine or the like), so as to create a high surface concentration of amino groups The material thus obtained is reacted with hyaluronic acid, a derivative thereof, or a semisynthetic polymer (e.g., (other polysaccharides containing carboxyl groups), in the presence of condensing agents such as EDC, in aqueous solution or dicyclohexylcarbodiimide (DCC) , in organic solvents. A molecule able to enhance the reaction promoted by EDC is also present. This class of molecule includes, but is not limited to, N-hydroxysuccinimide (NHS), hydroxy-sulfosuccinimide, hydroxybenzotriazolo hydrate and similar molecules.

Process B of the present invention is based on the surprising observation that molecules such as NHS are able to contribute to the condensation reaction promoted by EDC, also in the case of where groups are bound on the surface in the absence of molecular structures known by those skilled in the art as "spacer arms".

As far as hyaluronic acid, in particular, is concerned, it is known that, in solution, and in the absence of NHS, intermediate reaction products are formed, generically defined as N-acylurea, which prevent the reaction from being complete (X. Xu et al., Trans IV World Biom. Cong., 170, 1992). When the amino groups are bound to the surface, "spacer arms" must be used to render them sufficiently reactive. A "spacer arm" is a sequence of carbon atoms which separates the reactive group from the surface, thus making it freer and increasing its reactivity. For example, the product COVALINK (Nunc) is made of polystyrene containing secondary amino groups separated from the surface by a spacer arm with nine carbon atoms (K. Gregorius et al.; J. Immunol. Meth., 181, 65, 1995) and NHS proves efficacious in increasing the yield of the reaction promoted by EDC (J. V. Staros et al., Anal. Biochem., 156, 220, 1986). obviously, the cost of creating complex molecular structures on the surface, such as functional groups supported by spacer arms, is very high and limits the production process. In Process B of the present invention, the amino groups are bound to the surface and inside the PEI structure, without requiring the use of spacer arms or to attend to any other structural aspects. The finding that NHS is able to favor the condensation reaction of surface amino groups brought about by EDC, even in the absence of a spacer arm and without any particular attention being paid to other molecular aspects of the surface, is surprising and is a decisive factor in Process B of the invention.

Even more surprising and unforeseeable on the basis of previous knowledge is the finding that the presence of NHS in the reaction mixture has a decisive effect on the cellular antiadhesion properties of surfaces coated with hyaluronic acid or its derivatives. Indeed, when working in the absence of NHS, as described in U.S. Pat. No. 5,409,696, it is impossible to give the surfaces coated with hyaluronic acid antiadhesive properties to prevent the adhesion of cells. On the other hand, by working according to the processes of the present invention, surfaces are obtained which are perfectly resistant to cell colonization. Although the inventors are not obliged to explain the reasons for the results they obtained, and they do not intend to limit themselves to any one theory, it is supposed that the difference in behavior can be ascribed to one of the following reasons: either, in the absence of NHS, the yield of the reaction is too low, so that although the hyaluronic acid does bind to the surface it does not do so in a sufficient quantity to completely coat the underlying material; or the bond which is established in the absence of NHS alters the characteristics of the hyaluronic acid bound to the surface. The resulting structure does not maintain the properties which would normally be expected of this kind of polymer on the basis of common chemical knowledge.

In one particularly favorable form of the present invention, a polymeric, metal or ceramic material is treated with plasma of air or oxygen, with a power charge of between 1 and 400 W, preferably between 10 and 150 W, a pressure between 10 mtorr and 10 torr, and a treatment time between 1 second and 1 hour, preferably between 10 seconds and 30 minutes. However, the conditions of the treatment are not limiting and depend upon the shape of the product. The treatment takes longer if it involves modifying the inside of tubes or other inaccessible parts, while flat or exposed surfaces require shorter times.

The treated material is placed in an aqueous solution of PEI, at a concentration of between 0.01% and 10%, and preferably between 0.5% and 2%. The reaction time is not limiting and lasts between 10 minutes and 10 hours. At the end of this step, the material is washed and placed in a solution of hyaluronic acid or a derivative thereof or another polysaccharide containing carboxy groups. The concentration of the polysaccharide is between 0.005 and 5%, preferably between 0.05 and 1%. The solution is supplemented with NHS and EDC, at a concentration of between 0.001 and 1%. The reaction is achieved at room temperature or perhaps slightly heated and may last between 10 minutes and 48 hours. If the type of polysaccharide and the substrate are suitable, the reaction can be achieved in an organic solvent, using DCC and NHS at the previously specified concentrations.

The importance of this invention (Process A and B) will be evident to any expert in the field. Indeed, by the method of the present invention it is possible to obtain objects with favorable surface characteristics due to the presence of a coating of hyaluronic acid or a derivative thereof, remaining stable in time because of the presence of chemical bonds between the coating and the substrate. The surfaces of these objects, moreover, present marked characteristics of resistance to the adhesion of cells and bacteria present in the biological fluids.

We cite hereafter some purely illustrative examples and any variations which may be obvious to an expert in the field come within the scope of the present invention.

PREPARATION EXAMPLES

Example 1

A sample of polystyrene is taken from a bacteriological-grade Petri dish (Corning) and treated with plasma in a parallel-plate reactor (Gambetti Kenologia). The treatment is performed at a pressure of 100 mtorr of oxygen, a power charge of 50 W, a flow rate of 20 $cm^3$ (Std)/min and a treatment time of 30 seconds. The treated samples are immersed for two hours in a 0.5% solution of PEI (Aldrich) in water. They are then extracted, washed with water and immersed in test tubes containing 5 mL of the following solutions:

1) 1% (in weight) of hyaluronic acid (Fidia Advanced Biopolymers, Brindisi)

2) 1% (in weight) of hyaluronic acid, 0.02 g of 1-ethyl-3-(3-dimethylaminopropyl) carbodiimide (Sigma), 0.02 g of N-hydroxysuccinimide (Sigma).

3) 1% (in weight) of hyaluronic acid 25% esterified with benzyl alcohol (Fidia Advanced Biopolymers).

4) 1% (in weight) of hyaluronic acid 25% esterified with benzyl alcohol (Fidia Advanced Biopolymers), 0.02 g of 1-ethyl-3-(3-dimethylaminopropyl)-carbodiimide (Sigma), 0.3 g of N-hydroxysuccinimide (Sigma).

5) 1% (in weight) of hyaluronic acid 50% esterified with benzyl alcohol (Fidia Advanced Biopolymers).

6) 1% (in weight) of hyaluronic acid 50% esterified with benzyl alcohol, 0.02 g of 1-ethyl-3-(3-dimethylaminopropyl)carbodiimide (Sigma), 0.02 g of N-hydroxysuccinimide (Sigma).

The samples are left to stand in the test tubes at room temperature for 12 hours, after which they are washed in water overnight. The efficacy of the treatment is assessed by ESCA analysis (Electron Spectroscopy for Chemical Analysis). As is already known (Garbassi F. et al., "Polymer Surfaces, from Physics to Technology", Wiley, Chichester, 3, 1994), by this technique it is possible to assess the chemical composition of the surfaces of materials. Analysis is performed with a Perkin Elmer PHI 5500 ESCA system. Besides the previously described samples, another sample treated with plasma is used as a reference by placing it into contact with PEI alone.

| SURFACE COMPOSITION ATOMIC % | | | |
|---|---|---|---|
| Sample No. | O | C | N |
| 1 | 11.8 | 79.3 | 7.1 |
| 2 | 26.4 | 65.5 | 7.1 |
| 3 | 11.5 | 78.9 | 7.6 |
| 4 | 23.2 | 67.4 | 6.0 |
| 5 | 11.8 | 79.0 | 7.3 |
| 6 | 21.6 | 69.0 | 6.8 |
| PEI Alone | 11.2 | 78.8 | 7.5 |

Figure 1B:
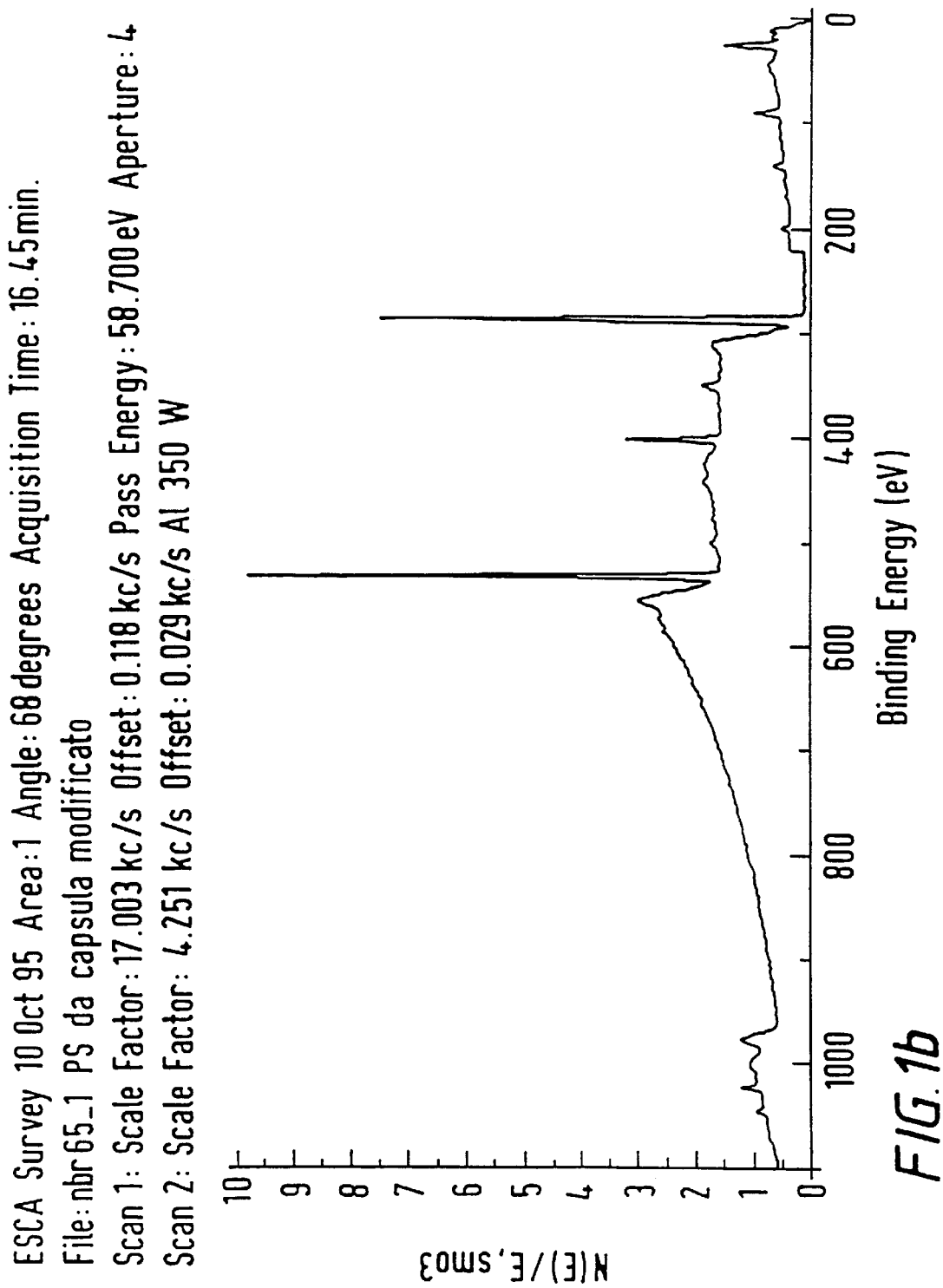
FIG. 1b: ESCA spectrum of sample 2, Example 1

These data show a marked increase in the quantity of oxygen present on the surface following the modification process, as expected after the introduction of hyaluronic acid or esters thereof. On the other hand, in the absence of EDC and NHS, the surface composition remains similar to the reference one. Moreover, detailed analysis of the Cls peak shows an abundance of C—O bonds, in accordance with the expected molecular structure. The ESCA spectra of samples 1 and 2 are reported in FIGS. 1a and 1b.

Example 2

Other samples prepared according to the process described in Example 1 are immersed in water for two months. ESCA analysis is repeated. No decreases or alterations in the surface concentration of oxygen are observed, thus confirming the stability of the bond between polysaccharide and surface.

Example 3

A film of polyethylene, as used for packaging, is treated with plasma and immersed in PEI as described in example 1. Two samples are prepared and immersed in the following solutions of dimethylsulfoxide (Fluka):

1) 1% of hyaluronic acid 75% esterified with benzyl alcohol (Fidia Advanced Biopolymers).

2) 1% of hyaluronic acid 75% esterified with benzyl alcohol 0.02 g of 1-ethyl-3-(3-dimethylaminopropyl) carbodiimide, 0.02 % of N-hydroxysuccinimide.

After washing in dimethylsulfoxide for 24 hours, the samples are analyzed by ESCA. The following results are obtained:

| SURFACE COMPOSITION ATOMIC % | | | |
|---|---|---|---|
| Sample No. | O | C | N |
| 1 | 11.8 | 79.3 | 7.1 |
| 2 | 21.4 | 69.5 | 6.4 |
| PEI alone | 11.2 | 78.8 | 7.5 |

Example 4

Figure 2A:
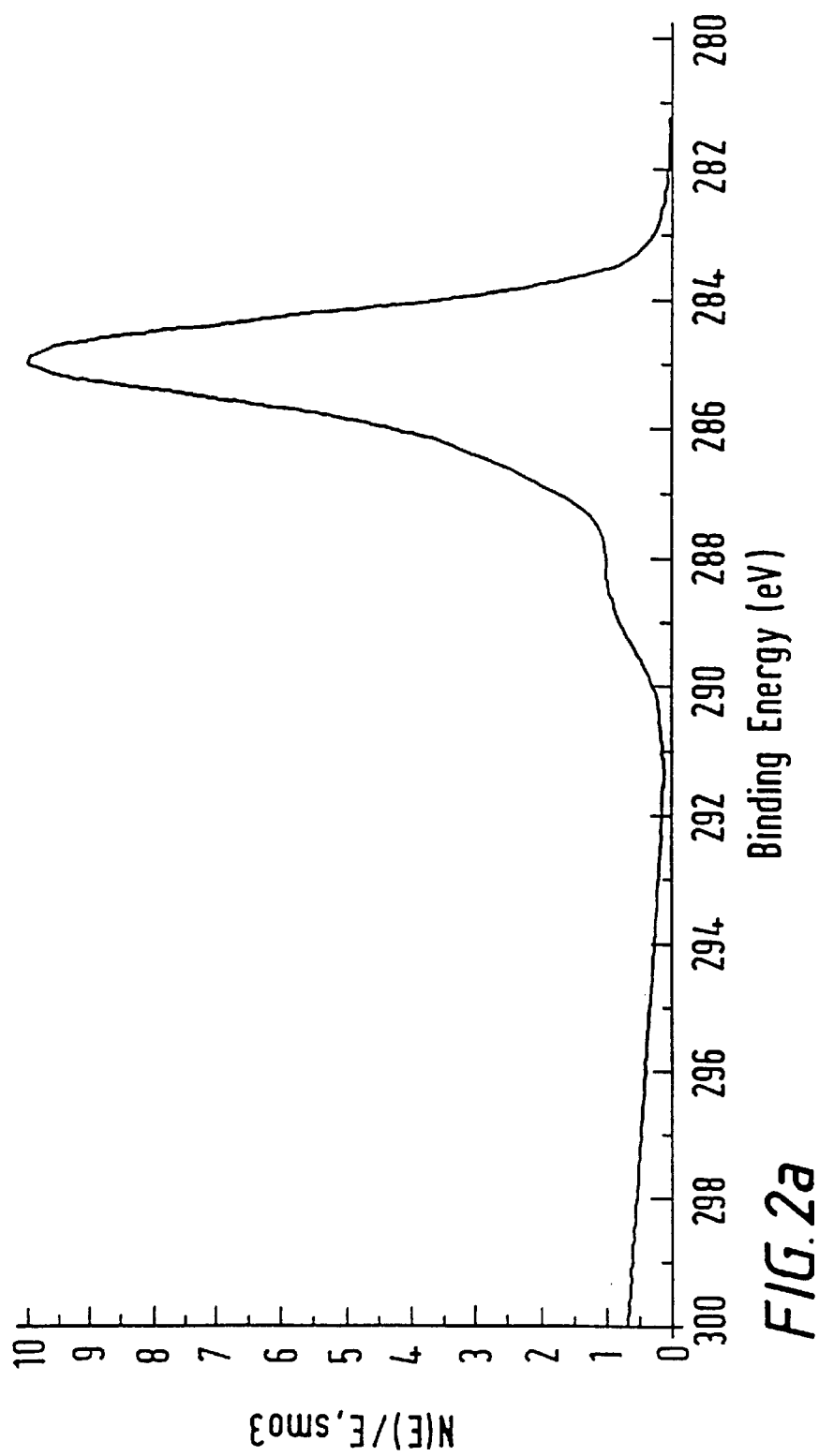
FIG. 2a: Cls peak obtained by ESCA analysis of the sample of steel placed in PEI solution
Figure 2B:
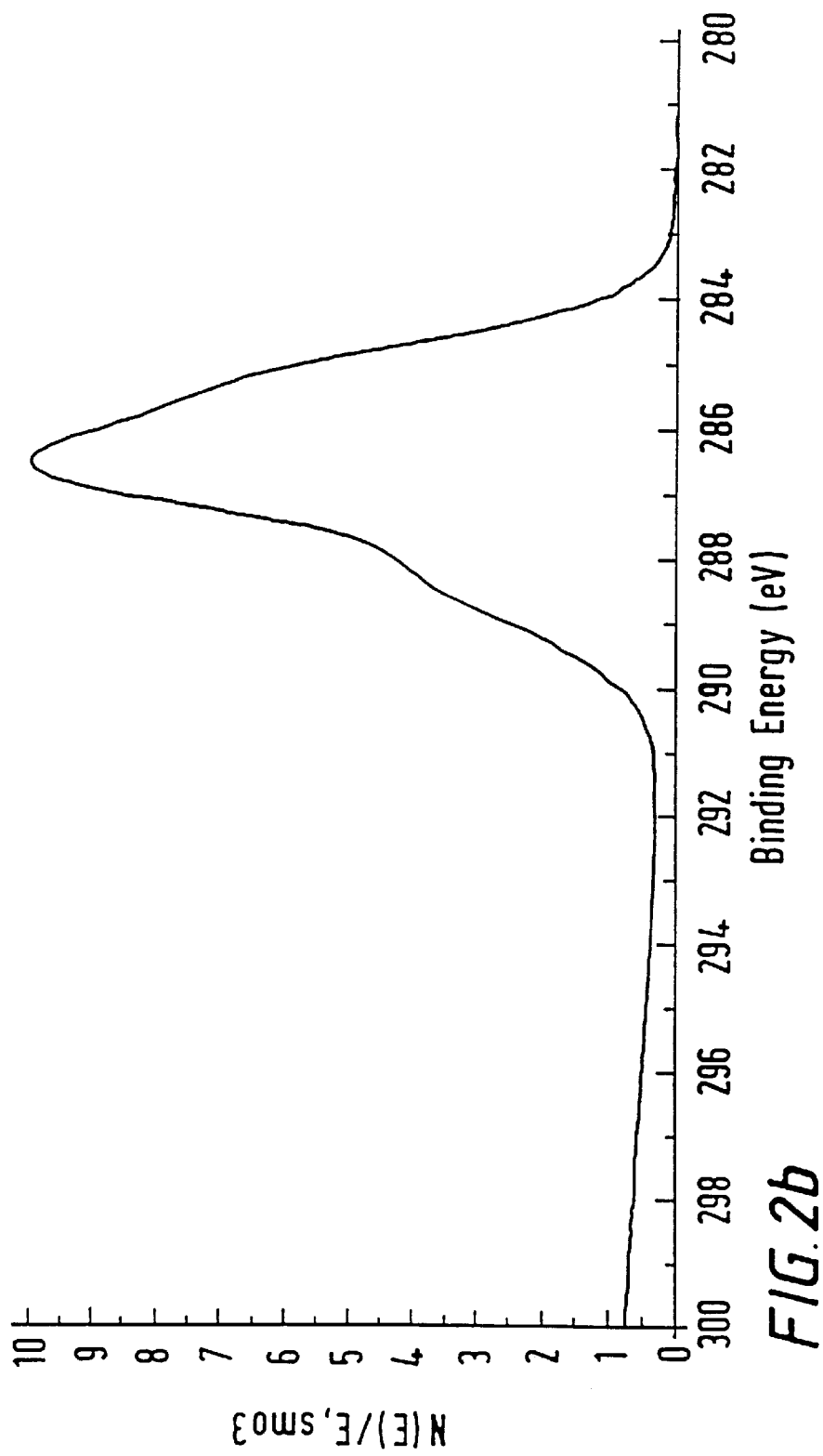
FIG. 2b: Cls peak obtained by ESCA analysis of the sample of steel modified with hyaluronic acid as described in Example 4

A sample of 316 steel, of a type commonly used for biomedical applications, is treated with air plasma for 15 minutes, then placed in contact with a solution of 0.5% PEI for 2 hours. Hyaluronic acid is bound to the surface of the material using solution 2 described in example 1. The material is then analyzed by ESCA analysis. The Cls peak obtained is reported in FIG. 2: FIG. 2a refers to the sample after exposure to a solution of PEI, FIG. 2b illustrates the Cls peak of the sample which underwent complete modification. In this last case the typical wide, multicomponent shape can be observed, characteristic of the Cls peak of polysaccharides (see, for example, the previously cited article by E. Ostenberg et al., Journal of Biomedical Materials Research, 29, 741, 1995), confirming the presence of hyaluronic acid on the surface.

Example 5

Petri dishes for cell culture (Corning) are modified as described in Example 1 (3 dishes per treatment). The dishes thus prepared are filled with 5 mL of cell suspension (fibroblast cells of mouse connective tissue, L-929 in Minimum Essential Eagle's medium, supplemented with 10% foetal calf serum, the antibiotics penicillin, streptomycin and amphotericin B and L-glutamine—SPA, Milan), placed in an incubator (Forma) at 37° C. at an atmosphere of 5% $CO_2$ and 98% humidity. The cell-to-cell interactions and the polystyrene base, treated as reported in Example 1, are assessed at regular intervals by optical phase-contrast microscope (Leica). In particular, we assessed whether the cells were able to adhere to differently treated supports, and to what extent, using as a control a Petri dish which had been treated with plasma alone, thereby having maximum adhesive properties. In this example (deriving from the mean of the observations conducted over a 24-hour period), a score of 5 refers to maximum adhesion, while score 0 signifies absence of adhesion.

| SAMPLE NO. | SCORE |
|---|---|
| CONTROL | 5 |
| 1 | 4 |
| 2 | 0 |
| 3 | 4 |
| 4 | 0 |
| 5 | 4 |
| 6 | 0 |

The experiment confirms the presence of a hydrophilic layer, firmly bound and able to prevent cell adhesion.

Example 6

Four polystyrene Petri dishes are treated according to the modification process described in Example 1, using solution 2 of hyaluronic acid (these samples will be referred to as A). An equal number of dishes is treated according to the hyaluronic acid coating process described in example 11 of U.S. Pat. No. 5,409,696 (these samples will be referred to as B). The modified dishes are placed in contact with a suspension of L929 cells, as described in the previous example. Cell adhesion is assessed as in the previous example and the results are as follows:

| SAMPLE | SCORE |
| --- | --- |
| Control | 5 |
| A | 0 |
| B | 4 |

Figure 3A:
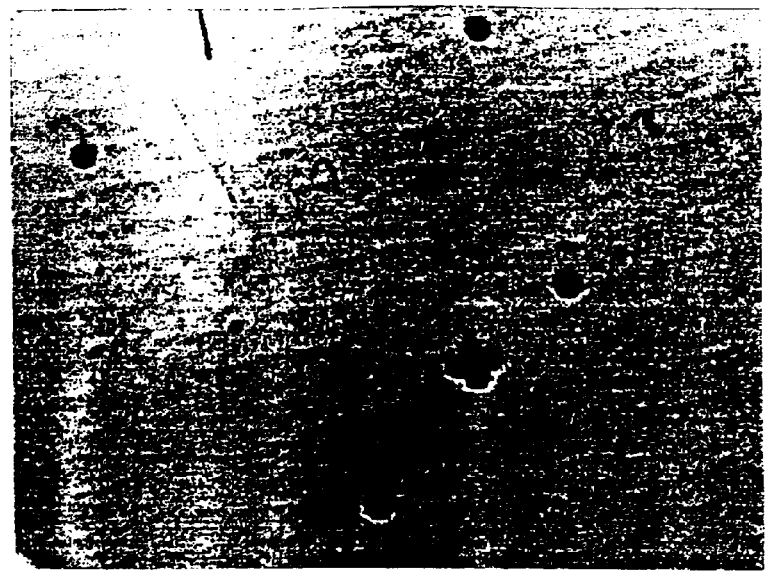
FIG. 3a: Optical microscope image showing non-adhesion of L-929 fibroblasts on the surface of sample A, Example 6 (200× enlargement)
Figure 3B:
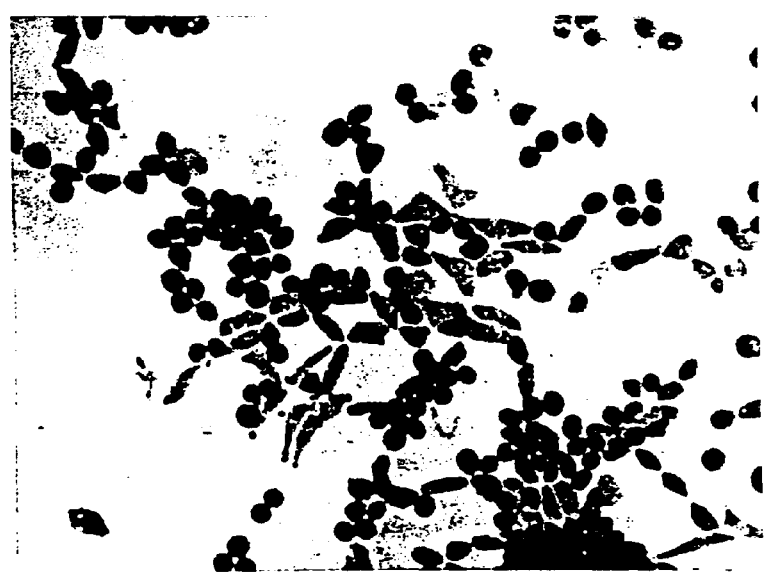
FIG. 3b: Optical microscope image showing adhesion of L-929 fibroblasts on the surface of sample B, Example 6 (200× enlargement)

FIGS. 3a and 3b are the images obtained with an optical microscope and show the state of the surfaces at the end of the test. FIG. 3a refers to sample A, 3b to sample B. The different degree of resistance to cell adhesion obtained by the two processes is clearly evident.

Example 7

Four polystyrene Petri dishes are treated according to the modification process described in example 1, using the solutions of hyaluronic acid esters 4 and 6 (these samples will be referred to as C and D respectively). An equal number of dishes is treated according to the hyaluronic acid coating process described in U.S. Pat. No. 5,409,696 using the same hyaluronic acid esters (these samples will be referred to as E and F). The modified dishes are placed in contact with a suspension of L-929 cells, as described in the previous example. Cell adhesion is assessed as in the previous example and the results are as follows:

| SAMPLE | SCORE |
| --- | --- |
| Control | 5 |
| C | 0 |
| D | 0 |
| E | 5 |
| F | 5 |

Figure 4A:
FIG. 4a: Optical microscope image showing non-adhesion of L-929 fibroblasts on the surface of sample D, Example 6 (200× enlargement)
Figure 4B:
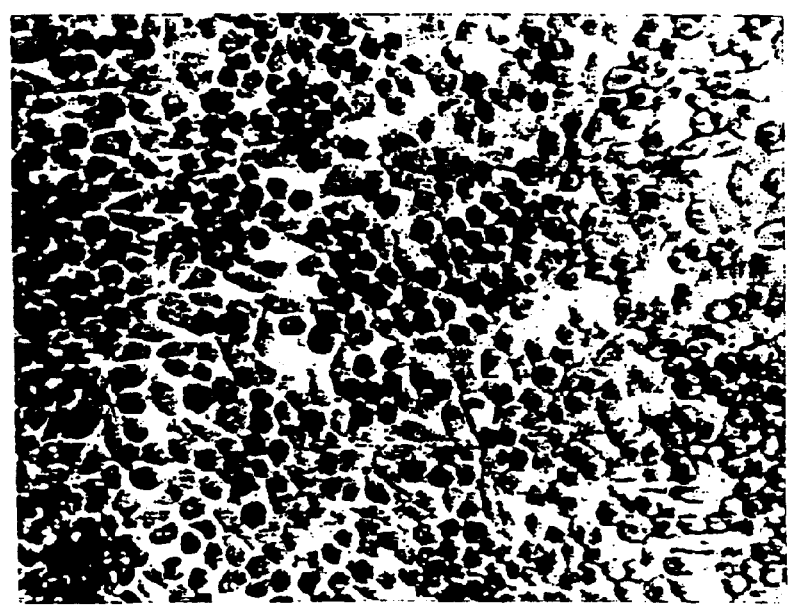
FIG. 4b: Optical microscope image showing adhesion of L-929 fibroblasts on the surface of sample F, Example 6 (200× enlargement)

FIGS. 4a and 4b are the images obtained with an optical microscope and show the state of the surfaces at the end of the test. FIG. 4a refers to sample D, 4b to sample F. The different degree of resistance to cell adhesion obtained by the two processes is clearly evident.

Example 8

Figure 5A:
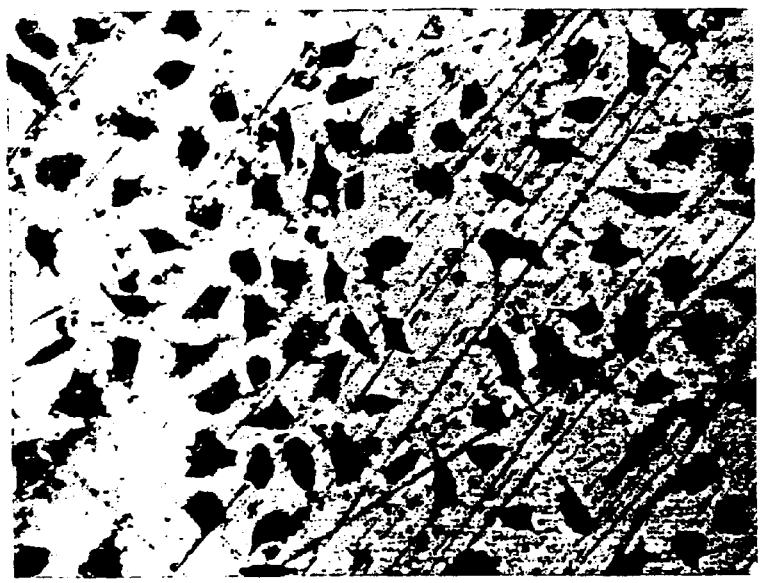
FIG. 5a: Optical microscope image showing adhesion of L-929 fibroblasts on the surface of titanium (200× enlargement)
Figure 5B:
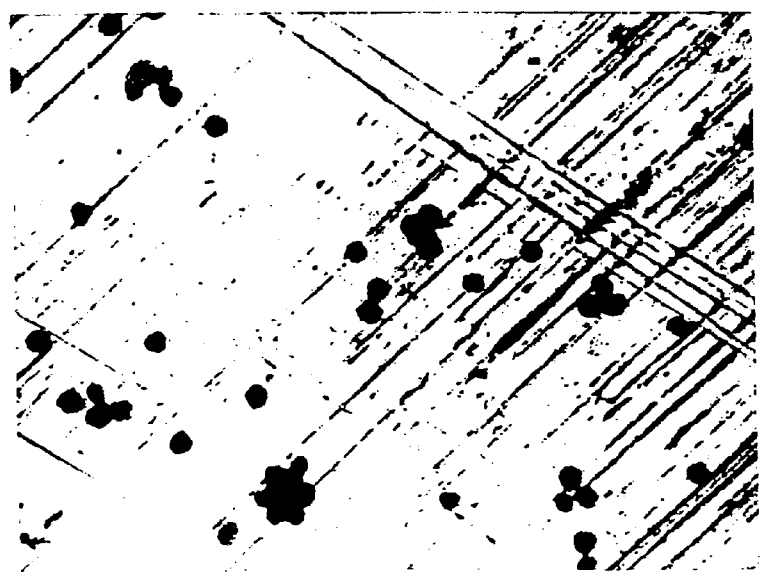
FIG. 5b: Optical microscope image showing non-adhesion of L-929 fibroblasts on the surface of titanium modified with hyaluronic acid ester, as described in Example 8 (200× enlargement)

A small sheet of titanium (Aldrich) is modified with plasma and treated with PEI as described in Example 4. The surface thus treated is reacted with solution 6 as in example 1. Four samples of unmodified titanium and four titanium samples which have undergone the modification process are placed in contact with a suspension of L-929 cells, as in the previous example. Cell adhesion is assessed 24 hours later, by coloring the cells with toluidine blue and observing the cultured samples with a metalographic microscope. The results of these observations are shown in FIGS. 5a and 5b. FIG. 5a refers to the unmodified titanium, FIG. 5b to titanium modified with hyaluronic acid ester according to the present process. It is evident that the cells behave differently on the two surfaces. In the case of the modified material, the cells maintain a rounded form and do not assume the flattened, spread appearance typical of cells which have adhered firmly to the substrate and as observed on the unmodified material (FIG. 5a).

Example 9

The modification process described in example 8 is performed on a glass slide. The modified glass, a sample of unmodified glass and a plasma-modified polystyrene dish (used as a control for its maximum adhesion) are placed in contact with L-929 cells. Cell adhesion is assessed 24 hours later. The following results are obtained:

| SAMPLE | SCORE |
| --- | --- |
| Control | 5 |
| Normal Glass | 5 |
| Modified Glass | 0 |

Example 10

Figure 6A:
FIG. 6a: Optical microscope image showing non-adhesion of L-929 fibroblasts on the surface of an intraocular lens modified with hyaluronic acid as described in Example 10 (50× enlargement)
Figure 6B:
FIG. 6b: Optical microscope image showing adhesion of L-929 fibroblasts on the surface of a non-modified intraocular lens (50× enlargement)
Figure 7A:
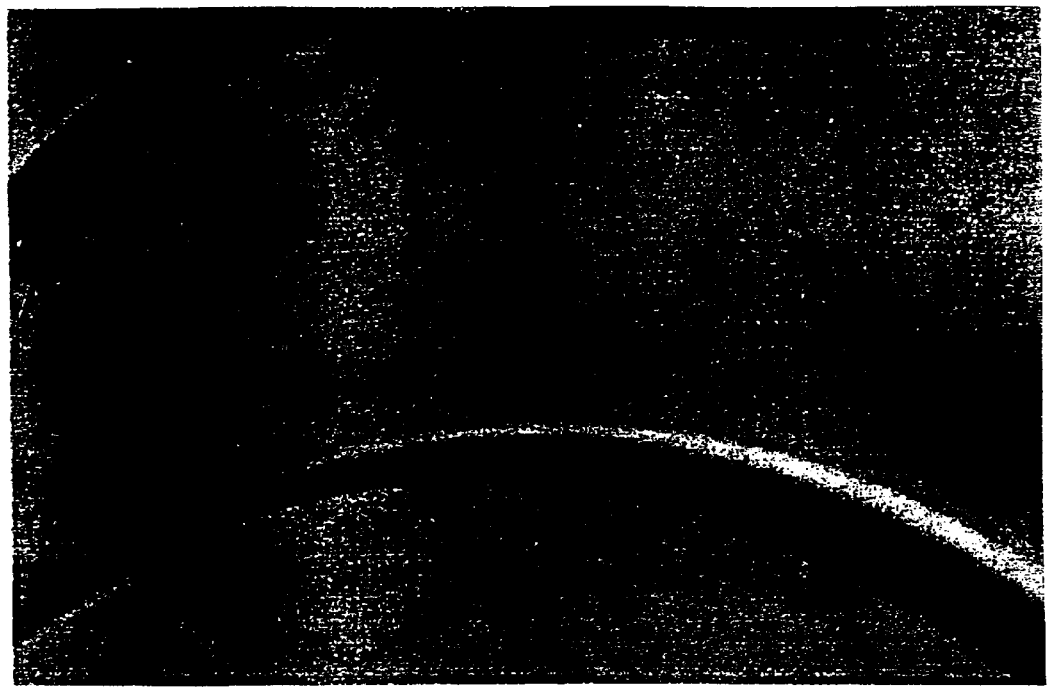
FIG. 7a: Optical microscope image showing non-adhesion of L-929 fibroblasts on the surface of an intraocular lens modified with hyaluronic acid, as described in Example 10 (200× enlargement)
Figure 7B:
FIG. 7b: Optical microscope image showing adhesion of L-929 fibroblasts on the surface of a non-modified intraocular lens (200× enlargement)

The modification process described in example 1 is performed on two intraocular lenses (Sanitaria Scaligera), using a solution of 0.5% ophthalmic-grade hyaluronic acid (Fidia Advanced Biopolymers), 0.4% of EDC and 0.4% of NHS. The modified lenses and an equal number of unmodified lenses are placed in Petri dishes and placed in contact with the suspension of L-929 cells, as in the previous examples. The samples' resistance to cell adhesion is illustrated in FIGS. 6 and 7. These are photographs of the surfaces of the lenses modified according to the present process (6a and 7a) and unmodified (6b and 7b). These figures clearly show the different capacity for cell adhesion inhibition of the two surfaces.

Example 11

A sample of polystyrene is taken from a bacteriological-grade Petri dish (Corning) and treated with plasma in a parallel-plate reactor (Gambetti Kenologia). The treatment is performed at a pressure of 100 mtorr of oxygen, a power charge of 100 W, a flow rate of 20 $cm^3$ (Std)/min and a treatment time of 1 minute. The treated samples are dipped and extracted five times in the following aqueous solutions, prepared 6 hours previously, and left to react at room temperature:

1) 1% hyaluronic acid (Fidia Advanced Biopolymers)

2) 1% (in weight) of hyaluronic acid, 0.4 g of 1-ethyl-3-(3-dimethylaminopropyl) carbodiimide (Sigma), 0.3 g of N-hydroxysuccinimide (Sigma), 1% (in volume) of 3-aminopropyltrimethoxy silane (Sigma).

3) 1% (in weight) of hyaluronic acid 25% esterified with benzyl alcohol (Fidia Advanced Biopolymers), 0.35 g of 1-ethyl-3-(3-dimethylaminopropyl) carbodiimide (Sigma) 0.3 g of N-hydroxysuccinimide (Sigma), 1% (in volume) or 3-aminopropyltrimethoxy silane (Sigma).

4) 1% (in weight) of hyaluronic acid 50% esterified with benzyl alcohol (Fidia Advanced Biopolymers), 0.35 g of 1-ethyl-3-(3-dimethylaminopropyl)-carbodiimide (Sigma), 0.3 g of N-hydroxysuccinimide (Sigma), 1% (in volume) of 3-aminopropyltrimethoxy silane (Sigma).

The samples are dried at 60° C. in an oven overnight and then washed in water and dried with a jet of compressed air. In order to check the integrity of the coating, the samples are immersed in a 1% solution of toluidine blue in water (Aldrich). This immediately stains hyaluronic acid and other polysaccharides a bright violet-blue. The efficacy of the process is assessed by assigning scores from a scale of 0 to 5, on which 5 corresponds to a perfectly even coloring (indicating the integrity of the coating of hyaluronic acid or derivative thereof) and 0 to the absence of staining. The samples prepared according to the example described (identified by the number of the solution in which they are immersed) score as follows:

| Sample | Score | Notes |
| --- | --- | --- |
| 1 | 1 | Staining appears homogenous at first, but the stained coating becomes detached after a few seconds in water. |
| 2 | 5 | |
| 3 | 5 | |
| 4 | 5 | |

Example 12

Some samples are prepared according to the method described in Example 11. The samples are immersed in water for 20 days at room temperature, after which the staining test is performed. The following results are obtained:

| SAMPLE NO. | SCORE |
| --- | --- |
| 1 | 0 |
| 2 | 5 |
| 3 | 5 |
| 4 | 4 |

Example 13

The following example allows the efficacy of the described process to be assessed, that is: the reaction between a polysaccharide and functional groups in solution, as opposed to the conventional approach involving a reaction between groups fixed to the surface and groups present in the polysaccharide. A silicone catheter is cut to obtain 3-cm long samples. A series of samples are treated according to the method described in Example 11, with solutions 2, 3 and 4. A second series of samples undergoes plasma treatment and application of 3-aminopropyltrimethoxy silane (Sigma), in a 1% (volume) aqueous solution. Once dry, the samples are placed in contact with the following solutions:

2a) 1% (weight) of hyaluronic acid, 0.4 g of 1-ethyl-3-(3-dimethylaminopropyl) carbodiimide (Sigma), 0.3 g of N-hydroxysuccinimide (Sigma).

3a) 1% (in weight) of hyaluronic 25% esterified with benzyl alcohol (Fidia Advanced Biopolymers), 0.351 g of 1-ethyl-3-(3-dimethylamiflopropyl) carbodiimide (Sigma), 0.3 g of N-hydroxysuccinimide (Sigma), 1%.

4a) 1% (in weight) of hyaluronic acid 50% esterified with benzyl alcohol (Fidia Advanced Biopolymers), 0.35 g of 1-ethyl-3-(3-dimethylaminopropyl)-carbodiimide (Sigma), 0.3 g of N-hydroxysuccinimide (Sigma).

The samples are dried at 60° C. in an oven overnight and then washed in water and dried with a jet of compressed air. The staining test gives the following results:

| SAMPLE NO. | SCORE |
| --- | --- |
| 2 | 5 |
| 3 | 5 |
| 4 | 5 |
| 2a | 1 |
| 3a | 0 |
| 4a | 0 |

Example 14

Bacteriological-grade polystyrene Petri dishes (Corning). are treated as described in Example 11 (3 dishes per treatment), using solutions 1, 2 and 3. The dishes thus prepared are filled with 5 ml of cell suspension (fibroblast cells of mouse connective tissue, L-929 in Minimum Eagle's Medium, to which 10% fetal calf serum, the antibiotics penicillin, streptomycin and amphotericin B and L-glutamine-SPA have been added), placed in an incubator (Forma) at 37° C. and an atmosphere of 5% $CO_2$ and 98% humidity. The cell-to-cell interactions and the polystyrene base, treated as reported in Example 11, are assessed at regular intervals by optical contrast-phase microscope (Leica) In particular, we assessed whether the cells were able to adhere to differently treated supports, and to what extent, using as a control a Petri dish which had been treated with plasma alone, thereby having maximum adhesive properties. In this example (deriving from the mean of the observations conducted over a 24-hour period), a score of 5 refers to maximum adhesion, while score 0 signifies absence of adhesion.

| SAMPLE NO. | SCORE |
| --- | --- |
| Control | 5 |
| 1 | 3 |
| 2 | 0 |
| 3 | 0 |

The experiment confirms the presence of a hydrophilic layer, firmly bound and able to prevent cell adhesion. This hydrophilic layer is removed from the sample treated with solution 1, which does not allow the formation of a chemical bond.

Example 15

A silicone catheter (Silkomed) is divided into sections each 7 centimeters long. Four samples are treated in the conditions described in Example 11, using solutions 1, 2, 3 and 4. The slipperiness of the catheters in an aqueous environment is assessed by the following method: a test tube is filled with Agar (Sigma) at a concentration of 0.7%. The test tube is fixed in a horizontal position and a 7-centimeter piece of catheter is placed inside it, with one end slightly protruding out of the Agar. A weight is attached to this extremity by means of a thread, which is then wound over a wheel so that the action of the weight pulls the catheter out of the Agar in which it is immersed. Because of Agar's particular characteristics, it is thus possible to assess the slippery properties of the catheter in an aqueous environment. The time it takes for the catheter to be extracted from the Agar is inversely proportional to the slipperiness of the catheter. The test gives the following results:

| SAMPLE NO. | EXTRACTION TIME (in Seconds) |
| --- | --- |
| 1 | 90 ± 13 |
| 2 | 35 ± 6 |
| 3 | 38 ± 8 |
| 4 | 36 ± 9 |
| plasma treatment only | 125 ± 15 |
| untreated | 120 ± 10 |

Example 16

The following example verifies a method using the action of plasma on the composition of the surface, which proves efficacious also on materials with different chemical compositions. Moreover, the example shows that the method is also effective when the object to be coated is composed of several different materials.

Three-centimeter lengths of catheter are prepared as samples. They are composed of a) silicon, b) polyurethane, c) polyvinyl chloride, d) rubber latex. A glass cover for microscope observation is also used. The samples are treated with plasma as described in Example 1, and then treated with solution 3 of the same Example, as described. The staining test gives the following results:

| MATERIAL | SCORE |
| --- | --- |
| Silicone | 5 |
| Polyurethane | 5 |
| Polyvinyl Chloride | 5 |
| Latex | 5 |
| Glass | 5 |

Example 17

A 1% solution of hyaluronic acid, 75% esterified with benzyl alcohol (Fidia Advanced Biopolymers) is prepared in dimethylsulfoxide (Aldrich). An aliquot of the solution is taken and to this is added 1.1% in volume of aminoethylaminopropyltrimethoxy silane and 0.5 g of dicyclohexylcarbodiimide (Aldrich). After reacting for 6 hours, two of the previously described samples of catheter are treated with plasma as described in Example 14. One of the samples is immersed in an ester solution, the other in an ester solution with amino silane, and extracted slowly. The samples are placed in a vacuum oven set at 60° C. and 100 torr and left there for 48 hours. The staining test gives the following results:

| SAMPLE | SCORE |
| --- | --- |
| Ester Solution | 1 |
| Ester Solution and Amino Silane | 4 |
| Plasma Only | 0 |
| Untreated | 0 |

Example 18

A 1% solution of hyaluronic acid, 50% esterified with ethyl alcohol (Fidia Advanced Biopolymers) in dimethylsulfoxide (Aldrich) is prepared. An aliquot of the solution is taken, and to this is added 1% in volume of aminoethylaminopropylmethoxy silane and 0.5 g of dicyclohexylcarbodiimide (Aldrich). After reacting for 6 hours, two samples of the aforesaid catheter are treated with plasma according to the conditions described in Example 14. One of the samples is immersed in an ester solution, the other in a solution of ester and amino silane, and they are slowly extracted. The samples are placed in a vacuum oven set at 60° C. and 100 torr and left there for 48 hours. The staining test gives the following results:

| SAMPLE | SCORE |
| --- | --- |
| Ester Solution | 1 |
| Ester Solution and Amino Silane | 5 |
| Plasma Only | 0 |
| Untreated | 0 |

Example 19

A 1% solution of hyaluronic acid 100% esterified with benzyl alcohol (Fidia Advanced Biopolymers) in dimethylsulfoxide (Aldrich) is prepared. An aliquot of the solution is taken, and to this is added 1% in volume of aminoethylaminopropyltrimethoxy silane and 0.5 g of carbonyldiimidazol (Aldrich). After reacting for 6 hours, two samples of the previously described catheter are treated with plasma according to the conditions in Example 14. One of the samples is immersed in the ester solution, the other in the solution of ester and amino silane, and they are slowly extracted. The samples are placed in a vacuum oven set at 60° C. and 100 torr and left there for 48 hours. The staining test gives the following results:

| SAMPLE | SCORE |
| --- | --- |
| Ester Solution | 1 |
| Ester Solution and Amino Silane | 4 |
| Plasma Only | 0 |
| Untreated | 0 |

Example 20

A 1% solution of hyaluronic acid, 100% esterified with ethyl alcohol (Fidia Advanced Biopolymers) in dimethylsulfoxide (Aldrich) is prepared. An aliquot of the solution is taken and to this is added 1% in volume of aminoethylaminopropyltrimethoxy silane and 0.5 g of carbonyldiimidazol (Aldrich). After reacting for 6 hours, two samples of the previously described catheter are treated with plasma according to the conditions in Example 14. One of the samples is immersed in the ester solution, the other in the solution of ester and amino silane, and they are slowly extracted. The samples are placed in a vacuum oven set at 60° C. and 100 torr and left there for 48 hours. The staining test gives the following results:

| SAMPLE | SCORE |
| --- | --- |
| Ester Solution | 1 |
| Ester Solution and Amino Silane | 4 |
| Plasma Only | 0 |
| Untreated | 0 |

Example 21

A 1% solution of cross-linked hyaluronic acid (10% of the carboxy groups involved in inner esterification—90% of the carboxy groups salified with sodium) in dimethylsulfoxide (Aldrich) is prepared. An aliquot of the solution is taken and to this is added it in volume of aminoethylaminopropyltrimethoxy silane and 0.5 g of dicyclohexylcarbodiimide (Aldrich). After reacting for six hours, two samples of the previously described catheter are treated with plasma according to the conditions in Example 4. One of the samples is immersed in the ester solution, the other in the solution of ester and amino silane, and they are slowly extracted. The samples are placed in a vacuum oven set at 60° C. and 100 torr and left there for 48 hours. The staining test gives the following results:

| SAMPLE | SCORE |
|---|---|
| Ester Solution | 1 |
| Ester Solution and Amino Silane | 5 |
| Plasma Only | 0 |
| Untreated | 0 |

Example 22

A 1% solution of alginic acid (50% of the carboxy groups esterified with benzyl alcohol—50% of the carboxy groups salified) in dimethylsulfoxide (Aldrich) is prepared. An aliquot of the solution is taken, and to this is added 1% in volume of aminoethylaminopropyltrimethoxy silane and 0.5 g of dicyclohexylcarbodiimide (Aldrich). After reacting for 6 hours, two samples of the previously described catheter are treated with plasma according to the conditions in Example 14. One of the samples is immersed in the ester solution, the other in the solution of ester and amino silane, and they are slowly extracted. The samples are placed in a vacuum oven set at 60° C. and 100 torr and left there for 48 hours. The staining test gives the following results:

| SAMPLE | SCORE |
|---|---|
| Ester Solution | 1 |
| Ester Solution and Amino Silane | 4 |
| Plasma Only | 0 |
| Untreated | 0 |

The aim of the present invention is therefore to provide new and innovative processes for the production of objects coated with a thin layer of hyaluronic acid or derivatives thereof or other semisynthetic polymers chemically bound to the substrate. Said processes can be applied to the manufacture of materials and devices with improved surface properties and, in particular, materials and devices characterized by hydrophilic surfaces. More specifically, the process can be used in the preparation of materials for biomedical and surgical applications, in urology, orthopaedics, otorhinolaryngology, gastroenterology, ophthalmology, in the cardiovascular sector and in diagnostics. For biomedical applications, devices for para- or extracorporeal use, such as catheters, blood bags, guide channels, probes, syringes, surgical instruments, containers, filtration systems; for prosthetic or surgical purposes or implants, it is possible to coat artificial tendons, joints, pins, cardiac valves, bone and cardiovascular replacements, grafts, venous catheters, intraocular lenses, soft tissue substitutes, etc. Examples of semipermanent devices which can be coated are contact lenses. Complex devices simulating physiological processes such as artificial kidneys, blood oxygenators, artificial hearts, pancreases, and livers. Lastly, in diagnostics, laboratory equipment, dishes for cell or tissue culture and/or regeneration and supports for active principles such as peptides, proteins and antibodies can be coated.

Each of the publications and patent documents cited and/or referred in the present specification are incorporated herein by reference in their entirety.

The invention being thus described, it is clear that these methods can be modified in various ways. Such modifications are not to be considered as divergences from the spirit and purpose of the invention and any such modification which would be apparent to an expert in the field comes within the scope of the following claims.

What is claimed is:

1. A process of coating a surface of an object with hyaluronic acid or a derivative thereof, which comprises the following steps:

reacting hyaluronic acid, or a derivative thereof, with an alkoxy silane coupling agent in an aqueous solution or an organic solvent, in the presence of a condensing or bifunctional agent, to give a solution containing the reaction product of the hyaluronic acid, or the derivative thereof, and the alkoxy silane coupling agent;

treating a surface of an object with a plasma;

coating the treated surface of said object with the solution containing the reaction product of the hyaluronic acid, or the derivative thereof, and the alkoxy silane coupling agent;

removing the solution from the surface of said object, while allowing said reaction product of the hyaluronic acid, or the derivative thereof, and the alkoxy silane coupling agent to react with said surface of the object.

2. A process according to claim 1, wherein the alkoxy silane coupling agent contains sulfhydryl groups or amino groups.

3. A process according to claim 1, wherein the alkoxy silane coupling agent is gamma-aminopropyltriethoxy silane or N-beta-(amino-ethyl)-gamma-aminopropyltrimethoxy silane.

4. A process according to claim 1, wherein the reaction between the alkoxy silane coupling agent and the hyaluronic acid, or the derivative thereof, occurs:

(i) in an aqueous solution in the presence of 1-ethyl-3-(3-dimethylaminopropyl)carbodiimide as said condensing agent; or (ii) in an organic solvent in the presence of dicyclohexylcarbodiimide as said condensing agent.

5. A process according to claim 1, wherein said reacting step is conducted in the presence of a compound which catalyzes or facilitates the reaction between the alkoxy silane coupling agent and the hyaluronic acid, or the derivative thereof.

6. A process of coating a surface of an object with a semisynthetic polymer, which comprises the following steps:

reacting a semisynthetic polymer with an alkoxy silane coupling agent in an aqueous solution or an organic solvent, in the presence of a condensing or bifunctional agent, to give a solution containing the reaction product of the semisynthetic polymer and the alkoxy silane coupling agent;

treating a surface of an object with a plasma;

coating the treated surface of said object with the solution containing the reaction product of the semisynthetic polymer and the alkoxy silane coupling agent;

removing the solution from the surface of said object, while allowing said reaction product of the semisynthetic polymer and the alkoxy silane coupling agent to react with said surface of the object.

7. A process according to claim 1 or 6, wherein said plasma is an oxygen plasma, an air plasma, a water plasma, an alcohol plasma, an acetone plasma, an oxygenated compound plasma, a nitrogen plasma, an argon plasma, or a mixture of two or more of said plasma.

8. A process according to claim 6, wherein the reaction between the semisynthetic polymer and the alkoxy silane coupling agent occurs:

(i) in an aqueous solution in the presence of 1-ethyl-3-(3-dimethyl-aminopropyl)carbodiimide as said condensing agent; or (ii) in an organic solvent in the presence of dicyclohexylcarbodiimide as said condensing agent.

9. A process according to claim 6, wherein said reacting step is conducted in the presence of a compound which catalyzes or facilitates the reaction between the semisynthetic polymer and the alkoxy silane coupling agent.

10. A process for coating the surface of an object with hyaluronic acid or a derivative thereof, which comprises the following steps:

treating a surface of an object with a plasma;

immersing the treated surface of the object in a solution containing polyethylene imine;

reacting the immersed treated surface of the object with hyaluronic acid, or a derivative thereof, in the presence of a carbodiimide and a substance selected from the group consisting of N-hydroxysuccinimide, hydroxysulfosuccinimide and hydroxybenzotriazolohydrate.

11. A process according to claim 1 or 10, wherein the hyaluronic derivative is:

(i) a total or partial benzyl ester of hyaluronic acid; or (ii) a total or partial ethyl ester of hyaluronic acid.

12. A process according to claim 10, wherein the reaction between the treated surface and the hyaluronic acid, or the derivative thereof, is achieved in:

(i) an aqueous solution in the presence of hydroxysuccinimide and 1-ethyl-3-(3-dimethylaminopropylcarbodiimide); or (ii) an organic solvent in the presence of hydroxysuccinimide and dicyclohexylcarbodiimide.

13. A process for coating the surface of an object with a semisynthetic polymer, which comprises the following steps:

treating a surface of an object with a plasma;

immersing the treated surface of the object in a solution containing polyethylene imine;

reacting the immersed treated surface of the object with a semisynthetic polymer, in the presence of a carbodiimide and a substance selected from the group consisting of N-hydroxysuccinimide, hydroxysulfosuccinimide and hydroxybenzotriazolohydrate.

14. A process according to claim 6 or 13, wherein the semisynthetic polymer is selected from the group consisting of:

an ester of a polyvalent alcohol of hyaluronic acid, an inner ester of an acidic polysaccharide, an ester of carboxymethylcellulose, an ester of carboxymethylchitin, an ester of carboxymethylamide, an active ester of a carboxylic polysaccharide, a sulfated ester of hyaluronic acid, an ester of alginic acid, an ester of chitin, an ester of chitosan, an ester of pectic, and an ester of pectinic acid.

15. A process according to claim 13, wherein the reaction between the treated surface and the semisynthetic polymer is achieved in:

(i) an aqueous solution in the presence of hydroxysuccinimide and 1-ethyl-3-(3-dimethylaminopropylcarbodiimide); or (ii) an aqueous solution in the presence of hydroxysuccinimide and dicyclohexylcarbodiimide.

16. A process according to claim 1, 6, 10 or 13, wherein the object to be coated comprises a material which is compatible with physiological fluids.

17. A process according to claim 10 or 13, wherein the object being coated comprises a polymeric material, a ceramic material or a metallic material.

18. A process according to claim 10 or 13, wherein object being coated comprises a metallic material selected from the group consisting of titanium, a titanium alloy, steel, and a chromium-cobalt alloy.

19. A process according to claim 1, 6, 10 or 13, wherein the object being coated is selected from the group consisting of:

catheters, blood bags, guide channels, probes, syringes, surgical instruments, containers, filtration systems, artificial tendons, joints, pins, cardiac valves, bone and cardiovascular replacements, grafts, venous catheters, intraocular lenses, contact lenses, soft tissue replacements, artificial kidneys, blood oxygenators, artificial hearts, pancreases and livers.

20. A process according to the claim 1, 6, 10 or 13, wherein the object being coated is selected from the group consisting of:

pieces of laboratory equipment, dishes for cell and tissue culture, dishes for cell and tissue regeneration, and supports for active principles that are peptides, proteins and antibodies.

21. A process according to claim 5, wherein said compound is N-hydroxysuccinimide, hydroxysulfosuccinimide or hydroxybenzotriazolohydrate.

22. A process according to claim 9, wherein said compound is N-hydroxysuccinimide, hydroxysulfosuccinimide or hydroxybenzotriazolohydrate.

* * * * *

UNITED STATES PATENT AND TRADEMARK OFFICE
CERTIFICATE OF CORRECTION

PATENT NO. : 6,129,956
DATED : October 10, 2000
INVENTOR(S) : Morra et al.

It is certified that error appears in the above-identified patent and that said Letters Patent is hereby corrected as shown below:

Page 1,
Field [86] § 371 Date: Please delete "Oct. 7, 1999" and insert -- Oct. 7, 1997 --
Field [86] § 102(e) Date: Please delete "Oct. 7, 1999" and insert -- Oct. 7, 1997 --

Signed and Sealed this

Twenty-first Day of August, 2001

Attest:

*Nicholas P. Godici*

NICHOLAS P. GODICI
*Attesting Officer*   *Acting Director of the United States Patent and Trademark Office*